United States Patent [19]

Umemoto et al.

[11] Patent Number: 5,368,852
[45] Date of Patent: Nov. 29, 1994

[54] PROLONGED-RELEASE LIQUID TYPE OF PHARMACEUTICAL PREPARATION COMPRISING DRUG-RESIN COMPLEX AND BENZOATE PRESERVATIVE

[75] Inventors: Mitsuo Umemoto, Osaka; Kiyotsugu Higashi, Gojo; Youko Mitani, Suita, all of Japan

[73] Assignee: Rohnto Pharmaceutical co., Ltd., Japan

[21] Appl. No.: 41,046

[22] Filed: Mar. 31, 1993

[30] Foreign Application Priority Data

Apr. 3, 1992 [JP] Japan ................... 4-081979

[51] Int. Cl.$^5$ .................. A61K 31/74; A61K 9/08
[52] U.S. Cl. .................. 424/78.1; 424/78.12; 424/78.13
[58] Field of Search ................ 424/78.1, 78.12, 78.13

[56] References Cited

U.S. PATENT DOCUMENTS

| | | | |
|---|---|---|---|
| 4,221,778 | 9/1980 | Raghunathan | 424/31 |
| 4,996,047 | 2/1991 | Kelleher et al. | 424/78.13 |
| 5,032,393 | 7/1991 | Douglas et al. | 424/78.13 |

FOREIGN PATENT DOCUMENTS

| | | |
|---|---|---|
| 0171528A | 5/1985 | European Pat. Off. . |
| 0294103A | 5/1988 | European Pat. Off. . |
| 0367746A | 10/1989 | European Pat. Off. . |
| 1908946 | 10/1969 | Germany .................. 424/78.12 |
| 0171528 | 2/1986 | Germany .................. 424/78.12 |
| 925890 | 5/1963 | United Kingdom ....... 424/78.12 |

*Primary Examiner*—Thurman K. Page
*Assistant Examiner*—Peter F. Kulkosky
*Attorney, Agent, or Firm*—Venable, Baetjer, Howard & Civiletti

[57] ABSTRACT

The present invention provides a prolonged-release liquid type of pharmaceutical preparation prepared by coating a pharmaceutically active drug-ion exchange resin complex which was treated previously with an impregnating agent, with a water permeable diffusion barrier material, followed by suspending the coated complex in a solution containing preservatives. The formulation of the present invention does not develop the rupture of the diffusion barrier film even in a solution containing preservatives. Therefore the formulation of the present invention is a prolonged-release liquid type of pharmaceutical preparation which is stable and does not lose the controlled release of the active ingredient.

15 Claims, 2 Drawing Sheets

PROLONGED-RELEASE LIQUID TYPE OF PHARMACEUTICAL PREPARATION COMPRISING DRUG-RESIN COMPLEX AND BENZOATE PRESERVATIVE

FIELD OF THE INVENTION

The present invention relates to a prolonged-release liquid type of pharmaceutical preparation. More particularly, the present invention relates to a prolonged-release liquid type of pharmaceutical preparation prepared by coating a pharmacologically active drug-ion exchange resin complex treated with an impregnating agent, with a diffusion barrier coating, followed by suspending the coated complex in a solution containing a preservative. In the pharmaceutical preparation of the present invention, the diffusion-barrier coating of the coated complex is not ruptured in a solution containing a preservative. Accordingly, the pharmaceutical preparation of the present invention is a stable prolonged-release liquid formulation whose controlled release of the active ingredient is assured for a prolonged period.

PRIOR ART

A method to release a drug using a complex of the drug with an ion exchange resin is known. In this method, a drug bound to an ion exchange resin via an ionic bond is administered, and then the drug in the form of an ion is exchanged with an ion existing in the body. A method in which a drug-ion exchange resin complex is coated with an insoluble polymer (diffusion barrier film) such as ethylcellulose in order to further sustain the release of the drug is also known. However, this coated complex suffers from the rupture of the diffusion barrier film since the ion exchange resin is swollen in water. U.S. Pat. Nos. 4,221,778 and 4,847,077 disclose a method in which an impregnating agent is used to prevent the rupture. In this method, a drug-ion exchange resin complex is treated with an impregnating agent such as polyethyleneglycol or glycerol, and then coated with ethylcellulose as a diffusion barrier material.

The ethylcellulose employed in the method mentioned above is prepared by reacting a major starting material such as purified pulps or cotton linter with ethylchloride to substitute OH group in glucose with ethoxyl group. The amount of ethoxyl group in ethylcellulose varies depending on the amount of ethylchloride to be reacted (when substituted completely, the content of ethoxyl group is 54.88%).

The content of ethoxyl group is limited to the range from 46.5 to 51.0% under Japanese standards of pharmaceutical ingredients, while it is limited to the range from 44.0 to 51.0% under National Formulary U.S.A.

When the complex coated with ethylcellulose as mentioned above is used in a liquid formulation, problems still remain although the problem of rupture of the diffusion barrier film due to swelling of the resin has been solved. Thus, the diffusion barrier film of a coated complex prepared using ethylcellulose having ethoxyl group in an amount within the specified range tends to be ruptured in the presence of a preservative frequently used to prepare a liquid formulation (a compound having antibacterial or antiseptic activity), whereby affecting the controlled release of the active ingredient and failing to obtain a clinically useful prolonged-release formulation.

For example, the complex prepared by treating a codeine-resin complex with polyethyleneglycol 4000 followed by coating the treated complex with ethylcellulose having the ethoxyl group content from 48.0 to 49.5% (Comparative 1) lost its controlled release property when placed in the solution of para-hydroxybenzoates or sodium benzoate which are used widely as preservatives in liquid formulations.

Observation of the coated complex by electron microscope revealed that the diffusion barrier film was ruptured after addition of the preservative although the film was consistent completely before addition of the preservative. Therefore, the addition of the preservative was considered to be attributable to the rupture of the diffusion barrier film which led to the lost of the controlled release of the drug.

When a preparation which lost the controlled release property is administered to humans, the excessive release of the drug (dose dumping) may occur, possibly causing serious side effects. Fluctuation of the release of the drug may also cause the fluctuation of the efficacy, making the formulation not desirable in a clinical stage.

Although a preservative may be added at a lower concentration in an attempt to prevent the rupture of the diffusion barrier film, reduced antibacterial or antiseptic effect may become another problem. In addition, as shown in the experiment described in this specification, the controlled release property is lost when the preservative was added at an effective concentration.

These results indicate that the liquid formulation containing a diffusion barrier-coated drug-resin complex and a preservative can not be stored for a long time and such formulation becomes far less valuable.

An object of the present invention is to provide a liquid formulation containing a diffusion barrier-coated drug-resin complex and a preservative which can be stored for a long time without change in release of the drug and which provides satisfactory release of the drug in the body. Thus, such formulation can be obtained first by reducing the loss of the controlled release property of the drug significantly by coating the drug-resin complex treated with an impregnating agent with a specific diffusion barrier film material, i.e. ethylcellulose having a specific content of ethoxyl group, and secondly by adding the specific preservative at a specific concentration to control the time course fluctuation in release of the drug.

In the prior arts mentioned above, no description of use of ethylcellulose having a specific content of ethoxyl group as a diffusion barrier film material can be found. There is no description of the effects of a preservative on stability of the diffusion barrier film of the complex or on control the drug release when the liquid formulation is made using the diffusion-barrier coated complex as mentioned above.

BRIEF DESCRIPTION OF THE INVENTION

Thus, the present invention provides a prolonged-release liquid type of pharmaceutical preparation characterized in that it contains in a suitable medium:

(a) 0.1–45.0 w/v % of diffusion barrier-coated complex particles, which is prepared by adsorbing a pharmacologically active drug onto ion exchange resin particles to form drug-resin complex particles, treating the drug-resin complex particles with an impregnating agent to form treated complex particles, and then coating the treated complex particles with ethylcellulose having 44.0–47.5% of ethoxyl group content; and (b) as a preservative, (i) one of para-hydroxybenzoic acid esters, wherein if methyl para-hydroxybenzoate is chosen, the preparation contains it at a concentration of 0.05–0.15 w/v %; if ethyl para-hydroxybenzoate is chosen, the preparation contains it at a concentration of 0.05–0.075 w/v %; if propyl para-hydroxybenzoate is chosen, the preparation contains it at a concentration of 0.03–0.05 w/v %; and if butyl para-hydroxybenzoate is chosen, the preparation contains it at a concentration of 0.01–0.015 w/v %;

(ii) a mixture of two or more of para-hydroxybenzoic acid esters, wherein if a mixture of methyl para-hydroxybenzoate and propyl para-hydroxybenzoate is chosen, the preparation contains the former at a concentration of 0.05–0.10 w/v % and the latter at a concentration of 0.01–0.02 w/v %, respectively; or (iii) sodium benzoate at a concentration of 0.1–0.5 w/v %.

As a dosage form of the preparation according to the present invention, a syrup for oral administration, nasal spray for nasal administration, and ophthalmic solution for instillation may be employed.

DETAILED DESCRIPTION OF THE INVENTION

Figure 1:
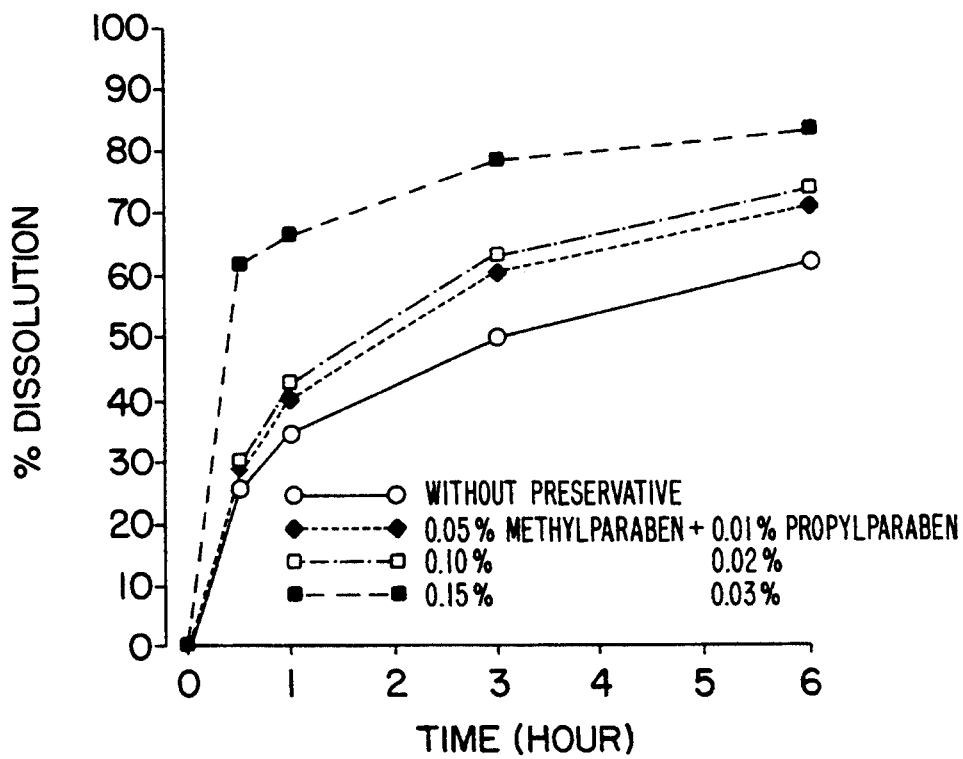
FIG. 1 is a graph showing the result of the dissolution test of the coated codeine-resin complex as the reference after storage in the solution of the mixture of methylparaben and propylparaben.

The pharmacologically active drug used in the present invention includes all medicinal compounds capable of being converted into ions. Preferable compounds in the present invention are, for example, codeine, dihydrocodeine, dextromethorphan, phenylpropanolamine, methylephedrine, hydrocodone and pilocarpine.

As an ion exchange resin used in the present invention, a cation exchange resin is used for a basic drug, while an anion exchange resin is used for a acid drug. In the examples described below, Amberlite IRP-69 (45–150 μm) which is a gel type divinylbenezene sulfonic acid cation exchange resin supplied from Röhm and Hass was used.

The impregnating agent used in the present invention includes polyethyleneglycol, polypropylene glycol, mannitol, lactose, methylcellulose, glycerol and the like. Polyethylene glycol is preferable, and polyethyleneglycol 4000 was used in the example. The amount of the impregnating agent is usually up to 30 parts by weight per 100 parts by weight of drug-resin complex.

A material for the diffusion barrier film is ethylcellulose having the content of ethoxyl group from 44.0 to 47.5%, preferably from 45.0 to 46.5%. A plasticizer such as Durkex 500 vegetable oil may also be incorporated to improve the film forming property.

Although the amount of ethylcellulose coating based on the drug-resin complex treated with the impregnating agent varies depending on the profile of drug release desired once the liquid formulation was administered, it should be within such a range that maintains the controlled release of the drug when admixed with a preservative while does not retard the release excessively. Thus, when the release of the drug is excessively retarded, then the drug is excreted before clinically effective dose is released and availability of the formulation is reduced. A preferable amount of ethylcellulose is usually 5.0 to 30.0 parts by weight per 100 parts by weight of impregnating agent-treated complex.

The concentration of the diffusion barrier-coated complex in the liquid formulation varies from 0.1 to 45.0 w/v % depending on the types of drug and solvent employed and the efficacy desired.

The preservative usually used in this field are various p-hydroxybenzoates, invert soaps, alcohol derivatives, organic acids and salts thereof, phenols, organic mercury compounds and the like. However, in the present invention, the preservative is preferably one or more p-hydroxybenzoates and sodium benzoate.

The maximum concentration of the preservative in the liquid formulation was selected so that the release of the drug does not change significantly when the drug is stored under the condition for aging at 60° C., while the minimum concentration was selected so that the antiseptic ability is maintained. Thus, the concentration of the preservative employed in the present invention is, for example, 0.05 to 0.15 w/v % when methyl p-hydroxybenzoate (methylparaben) is used, 0.05 to 0.075 w/v % when ethyl p-hydroxybenzoate (ethylparaben) is used, 0.03 to 0.05 w/v % when propyl p-hydroxybenzoate (propylparaben) is used, 0.01 to 0.015 w/v % when butyl p-hydroxybenzoate (butylparaben) is used, 0.05 to 0.10 w/v % and 0.01 to 0.02 w/v % when a mixture of methylparaben and propylparaben is used, and 0.1 to 0.5 w/v % when sodium benzoate is used. When a preservative other than listed above is employed, the concentration may be selected experimentally as shown in the examples according to the requirements mentioned above.

The solvent used to prepare the liquid formulation of the present invention may be an aqueous solvent. In addition to the preservative, a viscosity-increasing agent, a pH-adjusting agent, a sweetening agent and a flavoring agent may also be added to the solvent. As solvents other than the aqueous solvent, oily solvent such as vegetable oil, paraffin and glycols may also be employed, The formulation of the present invention can be prepared as follows. A pharmaceutical compound and an ion exchange resin are admixed in deionized water with stirring, washed thoroughly with deionized water in a Buchner funnel, and then dried in a fluidized-bed dryer to yield a drug-resin complex.

Then the drug-resin complex is treated with an impregnating agent. The treatment may be conducted according to the method disclosed in U.S. Pat. No. 4,221,778. In the examples of the present invention, polyethyleneglycol 4000 was used as the impregnating agent and dissolved in deionized water. The aqueous solution thus obtained was added to the drug-resin complex while stirring, and dried in a fluidized-bed dryer to yield an impregnating agent-treated drug-resin complex.

The complex thus obtained is then coated with a diffusion barrier film. The coating material listed above is dissolved in a suitable solvent (for example, ethanol, methylene chloride/acetone) and the solution is coated in an amount providing desired control of the release of the active ingredient onto the complex using a suitable coating method. In the examples of the present invention, methylene chloride:acetone (10:1) was used as the solvent and the solution was sprayed onto the complex using Wurster type coating apparatus to form a diffusion barrier film.

Finally, the coated complex thus obtained is suspended in a solvent containing a preservative to obtain a prolonged-release liquid formation of the present invention.

The formulation of the present invention has an excellent stability of the diffusion barrier film on the drug-resin complex, which is not broken even when stored for a long time. Accordingly it ensures the controlled release of the drug for a long time, providing a prolonged release of the drug after administration while keeping sufficient antiseptic property.

The present invention is further described in the following comparative, experiments and examples, which are not intended to limit the scope of the invention.

Comparative 1

Preparation of coated codeine-resin complex using ethylcellulose having the content of ethoxyl group from 48.0 to 49.5%.

A. Preparation of codeine-resin complex 95.0 g of codeine phosphate was dissolved in 950 ml of deionized water, and 359.9 g of Amberlite IRP 69 was added while stirring. The mixture was stirred for 1 hour. The codeine-resin complex was washed thoroughly in a Buchner funnel, and then dried in a fluidized bed drier for 1 hour at the inlet air temperature of 60° C. to yield a codeine-resin complex. B. Preparation of codeine-resin complex treated with polyethyleneglycol 82.5 g of polyethylene glycol (PEG) 4000 was dissolved in 104.8 ml of deionized water to form a PEG solution, which was added slowly to 350 g of the codeine-resin complex with stirring. After mixing for 15 minutes, the mixture was dried in a fluidized bed drier at the inlet air temperature of 40° C. for 1 hour to yield a PEG-treated codeine-resin complex.

C. Preparation of coating solution 45.0 g of ethylcellulose having the content of ethoxyl group from 48.0 to 49.5% and 21.2 g of Durkex 500 were dissolved in 130.4 g of acetone and 1304.0 g of methylene chloride to obtain a coating solution.

D. Preparation of coated codeine-resin complex

Using Wurster type coater at the inlet air temperature of 40° C., 998 g of the coating solution was sprayed continuously at the rate of 8 g/minute onto 400 g of the complex in such a manner that the coating amount of ethylcellulose+Durkex 500 based on the PEG-treated codeine-resin complex was 11.0 w/v %.

Experiment 1

(1) Preparation of samples 180 mg of the coated codeine-resin complex prepared in Comparative 1 was admixed with 1.0 ml of 1.3% polysorbate 80 in water, and the mixture was allowed to stand for 30 minutes. 12 ml of a solution of any one of methylparaben, ethylparaben, propylparaben and butylparaben, or 12 ml of a solution of the mixture of methylparaben and propylparaben was added to obtain the samples, which were allowed to stand overnight at 30° C. The samples were subjected to the dissolution test using a sample containing no preservatives as the control.

(2) Evaluation of dissolution

According to the dissolution test (paddle method) under Japanese Pharmacopeia of the 11th amendment (JPXI), 0.1 N HCl solution at 37° C. was used as the test solution to examine the effect of each preservative in the condition of the rotation of 100 rpm. Codeine was quantified by HPLC.

(3) Results

Dissolution rate of codeine when the coated codeine-resin complex prepared in Comparative 1 was stored in the solution of methylparaben or in the solution of propylparaben is shown in TABLE 1, while that when the complex was stored in the solution of the mixture of the both is shown in FIG. 1. Although the concentrations of the preservative in the solutions were antiseptically-effective concentrations, the controlled release of the drug of the complex which had been observed previously in the absence of the preservative was lost once stored overnight at 30° C.

Figure 2:
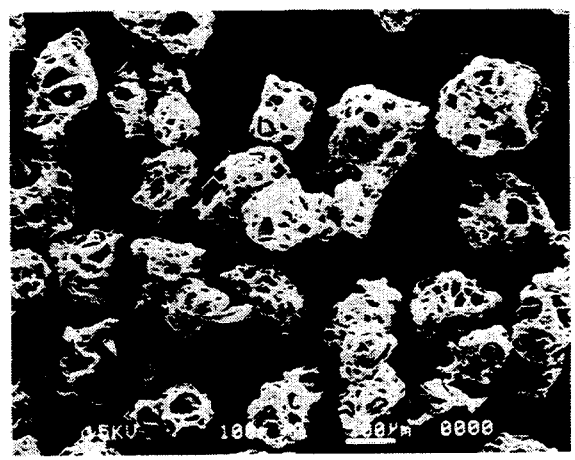
FIG. 2 is a photograph showing the structure of the particles of the coated codeine-resin complex as the reference after storage in the solution of the mixture of methylparaben and propylparaben.

When the coated codeine-resin complex stored in the solution of the mixture of methylparaben and propylparaben was observed by an electron microscope, the diffusion barrier film was broken (FIG. 2), indicating the loss of the controlled drug release.

The controlled release of the drug from the coated codeine-resin complex was lost similarly when the complex was stored in the solution of ethylparaben and in the solution of butylparaben.

TABLE 1

Change in % dissolution of drug from coated codeine-resin complex of the reference after storage in solution of methylparaben or in solution of propylparaben (30° C. for 1 day)

| Preservative | | time | | | |
|---|---|---|---|---|---|
| Type | Concentration (w/v %) | 0.5 hour | 1.0 hour | 3.0 hours | 6.0 hours |
| Without preservative | — | 25.9 | 34.6 | 49.6 | 61.6 |
| Methylparaben | 0.04 | 29.8 | 39.8 | 58.9 | 70.7 |
| | 0.08 | 31.0 | 40.7 | 60.5 | 71.0 |
| | 0.12 | 29.9 | 42.2 | 61.2 | 71.4 |
| | 0.16 | 31.0 | 43.7 | 61.6 | 70.5 |
| | 0.20 | 44.0 | 53.9 | 69.9 | 74.5 |
| Propylparaben | 0.010 | 28.9 | 41.5 | 57.4 | 69.0 |
| | 0.015 | 28.1 | 40.3 | 58.2 | 68.8 |
| | 0.020 | 28.8 | 41.2 | 59.0 | 69.3 |
| | 0.025 | 29.8 | 41.7 | 60.5 | 72.5 |
| | 0.030 | 30.4 | 43.1 | 60.1 | 71.1 |

Experiment 2

(1) Preparation and evaluation of samples 180 mg of the coated codeine-resin complex prepared in Comparative 1 was admixed with 1.0 ml of 1.3% polysorbate 80 in water, and the mixture was allowed to stand for 30 minutes. 12 ml of the solution of sodium benzoate was added and the mixture was allowed to stand at 30° C. overnight to obtain a sample, which was subjected to the dissolution test in the condition similar as in Experiment 1.

(2) Results

Dissolution rate of codeine when the coated codeine-resin complex prepared in Comparative 1 was stored in the solution of sodium benzoate at an effective concentration as a preservative is shown in TABLE 2. The results indicated that the controlled release of the drug from the complex which had been observed previously in the absence of the preservative was lost also when sodium benzoate was used as a preservative.

TABLE 2

Change in % dissolution of drug from coated codeine-resin complex of the reference after storage in solution of sodium benzoate (30° C. for 1 day)

| Preservative | | time | | | |
|---|---|---|---|---|---|
| Type | Concentration (w/v %) | 0.5 hour | 1.0 hour | 3.0 hours | 6.0 hours |
| Without preservative | — | 25.9 | 34.6 | 49.6 | 61.6 |
| Sodium benzoate | 0.1 | 32.4 | 43.6 | 60.0 | 71.1 |
| | 0.2 | 34.5 | 45.7 | 63.6 | 72.0 |
| | 0.3 | 37.1 | 47.2 | 64.7 | 73.5 |
| | 0.4 | 46.0 | 58.1 | 71.9 | 74.1 |
| | 0.5 | 70.5 | 75.1 | 80.4 | 86.2 |

EXAMPLE 1

Preparation of coated codeine-resin complex using ethylcellulose having content of ethoxyl group from 45.0 to 46.5%.

A. Preparation of codeine-resin complex 95.0 g of codeine phosphate was dissolved in 950 ml of deionized water, and 359.9 g of Amberlite IRP 69 was added while stirring. The mixture was stirred for 1 hour. The codeine-resin complex was obtained by the procedure similar as in Comparative 1.

B. preparation of codeine-resin complex treated with polyethylene glycol 82.5 g of PEG 4000 was dissolved in 104.8 ml of deionized water to form a PEG solution, which was added slowly to 350 g of the codeine-resin complex with stirring. After mixing for 15 minutes, the mixture was subjected to the procedure similar as in Comparative 1 to yield a PEG-treated codeine resin complex.

C. preparation of coating solution 45.0 g of ethylcellulose having the content of ethoxyl group from 45.0 to 46.5% and 21.2 g of Durkex 500 were dissolved in 130.4 g of acetone and 1304.0 g of methylene chloride to obtain a coating solution.

D. Preparation of coated codeine-resin complex

Using Wurster type coater at the inlet air temperature of 40° C., 998 g of the coating solution was sprayed continuously at the rate of 8 g/minute onto 400 g of the complex in such a manner that the coating amount of ethylcellulose+Durkex 500 based on the PEG-treated codeine-resin complex was 11.0 w/v %.

Example 2

(1) Preparation and evaluation of samples 180 mg of the coated codeine-resin complex prepared in Example 1 was admixed with 1.0 ml of 1.3% polysorbate 80 in water, and the mixture was allowed to stand for 30 minutes. 12 ml of any one of 0.30 w/v % methylparaben, 0.075 w/v % ethylparaben, 0.05 w/v % propylparaben and 0.015 w/v % butylparaben, or, 12 ml of the mixture of 0.15 w/v % methylparaben and 0.03 w/v % propylparaben was added. After allowed to stand at 30° C. overnight, the samples were subjected to the dissolution test in the condition similar as in Experiment 1.

(2) Results

Figure 3:
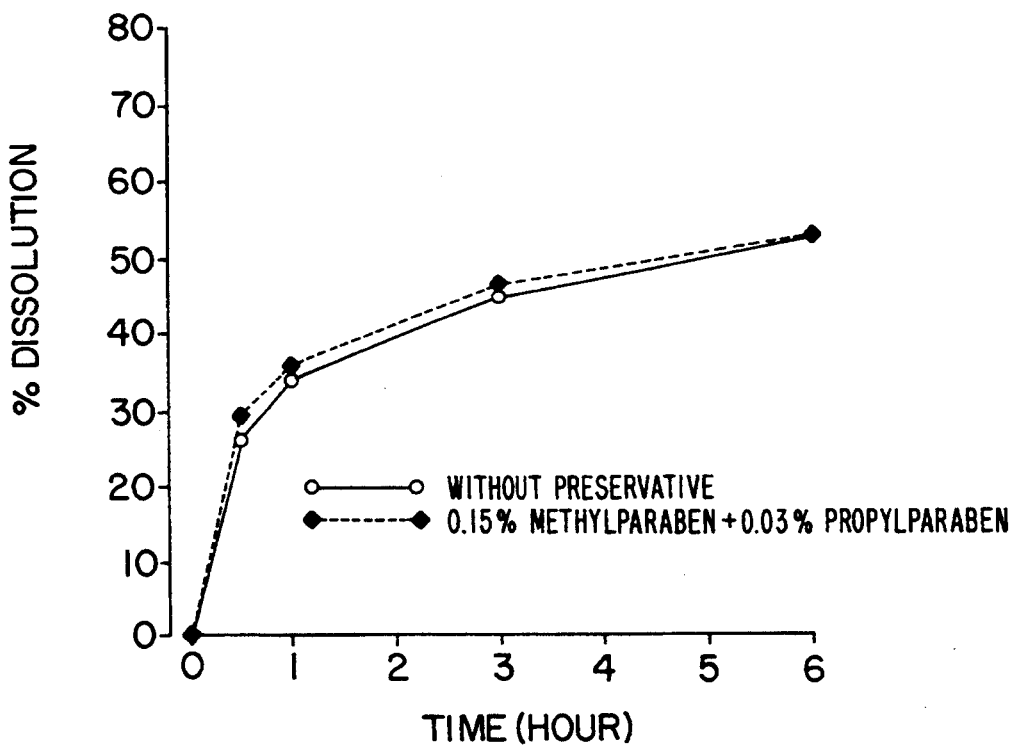
FIG. 3 is a graph showing the result of the dissolution test of the coated codeine-resin complex of the present invention after storage in the solution of the mixture of methylparaben and propylparaben.

Dissolution rate of codeine when the coated codeine-resin complex prepared in Example 1 was stored in the solution of any one of parabens in shown in TABLE 3, while that when the complex was stored in the solution of the mixture of the methylparaben and propylparaben is shown in FIG. 3. The results indicated that the dissolution rate of codeine in any of the solutions of the preservatives tested was similar to that observed in the sample containing no preservatives, showing that the controlled release of the drug from the complex was maintained.

Figure 4:
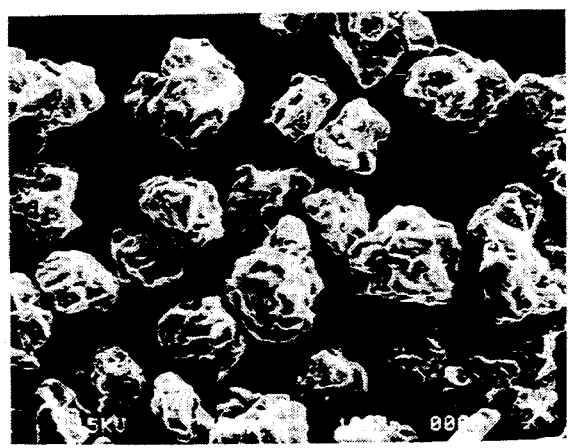
FIG. 4 is a photograph showing the structure of the particles of the coated codeine-resin complex of the present invention after storage in the solution of the mixture of methylparaben and propylparaben.

When the coated codeine-resin complex stored in the solution of the mixture of methylparaben and propylparaben was observed by an electron microscope, the diffusion barrier film coated the complex completely (FIG. 4).

TABLE 3

Change in % dissolution of drug from coated codeine-resin complex of Example 1 after storage in solution of any one of various parabens (30° C. for 1 day)

| Preservative | | time | | | |
|---|---|---|---|---|---|
| Type | Concentration (w/v %) | 0.5 hour | 1.0 hour | 3.0 hours | 6.0 hours |
| Without preservative | — | 23.3 | 31.1 | 45.3 | 53.8 |
| Methylparaben | 0.30 | 26.6 | 34.9 | 47.7 | 56.3 |
| Ethylparaben | 0.075 | 24.5 | 31.5 | 47.4 | 53.8 |
| Propylparaben | 0.05 | 25.0 | 33.7 | 46.3 | 54.6 |
| Butylparaben | 0.015 | 25.4 | 33.1 | 47.4 | 51.0 |

EXAMPLE 3

(1) Preparation and evaluation of samples 180 mg of the coated codeine-resin complex prepared in Example 1 was admixed with 1.0 ml of 1.3% polysorbate 80 in water, and the mixture was allowed to stand for 30 minutes. 12 ml of 0.9 w/v % solution of sodium benzoate was added and the mixture was allowed to stand at 30° C. overnight to obtain a sample, which was subjected to the dissolution test in the condition similar as in Experiment 1.

(2) Results

Dissolution rate of codeine when the coated codeine-resin complex prepared in Example 1 after storage in 0.9 w/v % solution of sodium benzoate was almost similar to that observed in the sample containing no preservatives, showing that the controlled release of the drug was maintained (TABLE 4).

TABLE 4

Change in % dissolution of drug from coated codeine-resin complex of Example 1 after storage in solution of sodium benzoate (30° C. for 1 day)

| Preservative | | time | | | |
|---|---|---|---|---|---|
| Type | Concentration (w/v %) | 0.5 hour | 1.0 hour | 3.0 hours | 6.0 hours |
| Without preservative | — | 26.1 | 33.8 | 44.8 | 52.5 |
| Sodium benzoate | 0.90 | 30.4 | 37.2 | 46.4 | 52.4 |

Example 4

(1) Preparation and evaluation of samples

The controlled release of the drug from the coated codeine-resin complex prepared in Example 1 was proved in Example 2 to be maintained even after the storage in aqueous solutions of various p-hydroxybenzoates overnight at 30° C. In this example, change in controlled release of the drug from the complex after storage in an aging condition was examined and the ranges of the concentrations of the preservatives were selected for the purpose of providing prolonged-release liquid type of pharmaceutical preparations exhibiting the controlled release of the drug which is not fluctuated over a long period.

Thus, 180 mg of the coated codeine-resin complex prepared in Example 1 was admixed with 1.0 ml of 1.3% polysorbate 80 in water, and the mixture was allowed to stand for 30 minutes. 12 ml of any one of the solutions of various p-hydroxybenzoate at various concentrations, namely, 0.05 to 0.30 w/v % methylparaben, 0.05 to 0.075 w/v % ethylparaben, 0.03 to 0.05 w/v % propylparaben and 0.01 to 0.015 w/v % butylparaben, or, 12 ml of the mixture of 0.05 to 0.20 w/v % methylparaben and 0.01 to 0.04 w/v % propylparaben was added. After allowed to stand at 60° C. for 5 days, the samples were subjected to the dissolution test in the condition similar as in Experiment 1.

(2) Results

Dissolution rate of codeine when the coated codeine-resin complex prepared in Example 1 was stored in the solution of any one of various parabens is shown in TABLE 5, while that when the complex was stored in the solution of the mixture of the methylparaben and propylparaben is shown in TABLE 6.

Based on the results, the maximum concentrations of the preservatives were so selected that the release of the drug was not changed markedly, while the minimum concentrations were so selected that the antiseptic effect could be maintained. Thus, 0.05 to 0.15 w/v % when methylparaben is used, 0.05 to 0.075 w/v % when ethylparaben is used, 0.03 to 0.05 w/v % when propylparaben is used and 0.01 to 0.015 w/v % when butylparaben is used were selected. When the mixture of methylparaben and propylparaben is used, the concentrations of 0.05 to 0.10 w/v % and 0.01 to 0.02 w/v %, respectively, were selected.

It was confirmed that there was almost no change in % dissolution of the drug when the complex was stored in the solutions of the preservatives at the concentrations within the ranges specified above at 25° C. for a long period.

TABLE 5

Change in % dissolution of drug from coated codeine-resin complex of Example 1 after storage in solution of any one of various parabens (60° C. for 5 days)

| Preservative | | time | | | |
|---|---|---|---|---|---|
| Type | Concentration (w/v %) | 0.5 hour | 1 hour | 3.0 hours | 6.0 hours |
| Without preservative | — | 23.3 | 31.1 | 45.3 | 53.8 |
| Methyparaben | 0.05 | 25.0 | 33.2 | 47.0 | 55.8 |
| | 0.10 | 26.4 | 34.0 | 47.3 | 55.5 |
| | 0.15 | 28.7 | 37.8 | 50.4 | 59.2 |
| | 0.20 | 33.7 | 42.3 | 53.8 | 60.6 |
| | 0.25 | 37.7 | 47.8 | 60.4 | 68.5 |
| | 0.30 | 43.7 | 53.2 | 67.1 | 73.8 |
| Ethylparaben | 0.05 | 27.8 | 35.9 | 47.6 | 57.4 |
| | 0.06 | 25.7 | 33.6 | 46.5 | 56.0 |
| | 0.07 | 25.7 | 34.4 | 46.3 | 55.7 |
| | 0.075 | 26.6 | 34.9 | 49.6 | 57.1 |
| Propylparaben | 0.03 | 25.0 | 34.4 | 45.2 | 55.9 |
| | 0.04 | 27.1 | 34.2 | 47.6 | 55.7 |

TABLE 5-continued

Change in % dissolution of drug from coated codeine-resin complex of Example 1 after storage in solution of any one of various parabens (60° C. for 5 days)

| Preservative | | time | | | |
|---|---|---|---|---|---|
| Type | Concentration (w/v %) | 0.5 hour | 1 hour | 3.0 hours | 6.0 hours |
| Butylparaben | 0.05 | 28.6 | 35.6 | 50.4 | 59.5 |
| | 0.010 | 25.0 | 33.0 | 45.2 | 55.0 |
| | 0.013 | 25.0 | 32.9 | 44.8 | 54.8 |
| | 0.015 | 26.0 | 34.8 | 47.9 | 56.9 |

TABLE 6

Change in % dissolution of drug from coated codeine-resin complex of Example 1 after storage in solution of mixture of methylparaben and propylparaben (60° C. for 5 days)

| Preservative | | time | | | |
|---|---|---|---|---|---|
| Methylparaben (w/v %) | Propylparaben (w/v %) | 0.5 hour | 1.0 hour | 3.0 hours | 6.0 hours |
| 0 (Without preservative) | 0 (Without preservative) | 26.1 | 33.8 | 44.8 | 52.5 |
| 0.05 | 0.01 | 25.8 | 33.1 | 43.8 | 49.6 |
| 0.10 | 0.02 | 29.5 | 35.4 | 46.5 | 52.6 |
| 0.15 | 0.03 | 35.5 | 41.9 | 52.3 | 58.6 |
| 0.20 | 0.04 | 39.5 | 48.8 | 61.5 | 65.1 |

EXAMPLE 5

(1) Preparation and evaluation of samples

The controlled release of the drug from the coated codeine-resin complex prepared in Example 1 was proved in Example 3 to be maintained even after the storage in the solution of sodium benzoate overnight at 30° C. In this Example, in order to select the range of concentration of sodium benzoate, 180 mg of the coated codeine-resin complex prepared in Example 1 was admixed with 1.0 ml of 1.3% polysorbate 80 in water, and the mixture was allowed to stand for 30 minutes, and then 12 ml of the solution of sodium benzoate at various concentrations (0.1 to 1.3 w/v %) was added and, after storage for 5 days at 60° C., subjected to the dissolution test in the condition similar as in Experiment 1.

(2) Results

Increase in % dissolution was observed with dependency on the concentration of sodium benzoate (TABLE 7). Based on the results, the range of the concentration of sodium benzoate from 0.1 to 0.5 w/v % was selected. The results of the long term storage test at 25° C. revealed that there was no change in % dissolution at the concentrations of the preservative within the range specified above.

TABLE 7

Change in % dissolution of drug from coated codeine-resin complex of Example 1 after storage in solution of sodium benzoate (60° C. for 5 days)

| Preservative | | time | | | |
|---|---|---|---|---|---|
| Type | Concentration (w/v %) | 0.5 hour | 1.0 hour | 3.0 hours | 6.0 hours |
| Without preservative | — | 26.1 | 33.8 | 44.8 | 52.5 |
| Sodium benzoate | 0.1 | 27.5 | 34.2 | 43.9 | 49.5 |
| | 0.5 | 33.9 | 39.1 | 47.5 | 55.6 |
| | 0.9 | 39.6 | 44.2 | 51.9 | 57.3 |
| | 1.3 | 44.1 | 48.1 | 54.4 | 60.4 |

EXAMPLE 6

Preparation of coated phenylpropanolamine (PPA)-resin complex using ethylcellulose having content of ethoxyl group from 45.0 to 46.5%

A. Preparation of PPA-resin complex 12.0 kg of PPA hydrochloride was dissolved in 120.0 kg of deionized water, and 45.0 kg of Amberlite IRP69 was added while stirring. The mixture was stirred for 1 hour. The PPA-resin complex was washed thoroughly in a Buchner funnel, and then dried in a fluidized-bed dryer for 1 hour at the inlet air temperature of 60° C. to yield a PPA-resin complex.

B. Preparation of PEG-treated PPA-resin complex 13.65 kg of PEG 4000 was dissolved in 21.8 kg of deionized water to form an aqueous solution of PEG, which was added slowly to 54.5 kg of PPA-resin complex with stirring. After mixing for 15 minutes, the mixture was dried in a fluidized-bed dryer at the inlet air temperature of 40° C. For 1 hour to yield a PEG-treated PPA-resin complex.

C. Preparation of coating solution 6.0 kg of ethylecellulose described above and 2.82 kg of Durkex 500 were dissolved in 17.38 kg of acetone and 173.8 kg of methylene chloride to obtain a coating solution.

D. Preparation of coated PPA-resin complex

Using Wurster type coating at the inlet air temperature of 40° C., 190 kg of the coating solution was sprayed continuously at the rate of 580 g/minute onto 60.0 kg of the complex in such a manner that the coating amount of ethylcellulose+Durkex 500 based on the PEG-treated PPA-resin complex was 14.0 w/w %.

EXAMPLE 7

(1) Preparation and evaluation of samples 750 mg of the coated PPA-resin complex prepared in Example 6 was admixed with 1.0 ml of 1.3% polysorbate 80 in water, and the mixture was allowed to stand for 30 minutes. 12 ml of the solution of the mixture of 0.10 w/v % methylparaben and 0.02 w/v % propylparaben was added and the mixture was allowed to stand at 30° C. overnight to obtain a sample, which was subjected to the dissolution test. A sample containing no parabens was used as a control.

(2) Results

Dissolution rate of PPA from the coated PPA-resin complex is shown in TABLE 8. The dissolution rate of the drug when the complex was stored in the solution of the mixed parabens was almost similar to that observed in the sample containing no parabens, showing that the controlled release of the drug was maintained. When the complex was after storage with parabens was observed by an electron microscope, the diffusion barrier film coated the complex completely.

TABLE 8

Change in % dissolution of drug from coated PPA-resin complex of Example 6 after storage in solution of mixture of methylparaben and propylparaben (30° C. for 1 day)

| Preservative Concentration (w/v %) | time | | | | |
| --- | --- | --- | --- | --- | --- |
| | 5 minutes | 15 minutes | 30 minutes | 1.0 hour | 2.0 hours |
| Without preservative | 24.2 | 36.8 | 50.5 | 59.6 | 67.9 |
| 0.10% methylparaben + 0.02% propylparaben | 22.6 | 39.4 | 50.6 | 61.8 | 69.3 |

EXAMPLE 8

Preparation of coated dihydrocodeine-resin complex using ethylcellulose having content of ethoxyl group from 45.0 to 46.5%

60.0 g of dihydrocodeine phosphate was dissolved in 600 ml of deionized water, and 378.8 g of Amberlite IRP 69 was added while stirring. The mixture was stirred for 1 hour to yield a dihydrocodeine-resin complex. Then, the complex was treated with PEG and coated with the diffusion barrier material similarly as in Example 1 to obtain a coated dihydrocodeine-resin complex.

EXAMPLE 9

Preparation of coated dextromethorphan-resin complex using ethylcellulose having content of ethoxyl group from 45.0 to 46.5%

90.0 g of dextromethorphan hydrobromide was dissolved in 900 ml of deionized water, and 378.8 g of Amberlite IRP69 was added while stirring. The mixture was stirred for 1 hour to yield a dextromethorphan-resin complex. Then, the complex was treated with PEG and coated with the diffusion barrier material similarly as in Example 1 to obtain a coated dextromethorphan-resin complex.

EXAMPLE 10

Preparation of coated methylephedrine-resin complex using ethylcellulose having content of ethoxyl group from 45.0 to 46.5%

75.0 g of methylephedrine hydrochloride was dissolved in 750 ml of deionized water, and 378.8 g of Amberlite IRP69 was added while stirring. The mixture was stirred for 1 hour to yield a methylephedrine-resin complex. Then, the complex was treated with PEG and coated with the diffusion barrier material similarly as in Example 1 to obtain a coated methylephedrine-resin complex.

EXAMPLE 11

Preparation of coated hydrocodone-resin complex using ethylcellulose having content of ethoxyl group from 45.0 to 46.5%

20.0 g of hydrocodone bitartarate was dissolved in 800 ml of deionized water, and 378.8 g of Amberlite IRP69 was added while stirring. The mixture was stirred for 1 hour to yield a hydrocodone-resin complex. Then, the complex was treated with PEG and coated with the diffusion barrier material similarly as in Example 1 to obtain a coated hydrocodone-resin complex.

EXAMPLE 12

Preparation of coated pilocarpine-resin complex using ethylcellulose having content of ethoxyl group from 45.0 to 46.5%

100.0 g of pilocarpine hydrochloride was dissolved in 900 ml of deionized water, and 300.0 g of Amberlite IRP69 was added while stirring. The mixture was stirred for 1 hour to yield a pilocarpine-resin complex. Then, the complex was treated with PEG and coated with the diffusion barrier material similarly as in Example 1 to obtain a coated pilocarpine-resin complex.

EXAMPLE 13

Syrup formulation for oral administration

A syrup formulation was prepared using the ingredients shown below.

| | |
|---|---|
| Coated codeine-resin complex of Example 1 | 1.57 g |
| Methylparaben | 0.10 g |
| Propylene glycol alginate | 1.40 g |
| Propylene glycol | 1.0 g |
| Corn syrup | 30.0 g |
| Citric acid | 0.1 g |
| Polysorbate 80 | 0.1 g |
| Deionized water | q.s. to 100 ml |

EXAMPLE 14

Syrup formulation for oral administration

A syrup formulation was prepared using the ingredients shown below.

| | |
|---|---|
| Coated PPA-resin complex of Example 6 | 3.22 g |
| Ethylparaben | 0.06 g |
| Tragacanth gum | 1.0 g |
| Propylene glycol | 1.0 g |
| Corn syrup | 30.0 g |
| Citric acid | 0.1 g |
| Polysorbate 80 | 0.1 g |
| Deionized water | q.s. to 100 ml |

EXAMPLE 15

Syrup formulation for oral administration

A syrup formulation was prepared using the ingredients shown below.

| | |
|---|---|
| Coated dihydrocodeine-resin complex of Example 8 | 1.45 g |
| Propylparaben | 0.04 g |
| Tragacanth gum | 1.0 g |
| Propylene glycol | 1.0 g |
| Corn syrup | 30.0 g |
| Citric acid | 0.1 g |
| Polysorbate 80 | 0.1 g |
| Deionized water | q.s. to 100 ml |

EXAMPLE 16

Syrup formulation for oral administration

A syrup formulation was prepared using the ingredients shown below.

| | |
|---|---|
| Coated dextromethorphan-resin complex of Example 9 | 2.03 g |
| Butylparaben | 0.013 g |
| Xanthane gum | 0.3 g |
| Propylene glycol | 1.0 g |
| High-maltose syrup | 40.0 g |
| Sorbitol | 20.0 g |
| Citric acid | 0.1 g |
| Polysorbate 80 | 0.1 g |
| Deionized water | q.s. to 100 ml |

EXAMPLE 17

Syrup formulation for oral administration

A syrup formulation was prepared using the ingredients shown below.

| | |
|---|---|
| Coated methylephedrine-resin complex of Example 10 | 4.84 g |
| Methylparaben | 0.10 g |
| Propylparaben | 0.02 g |
| Hydroxypropylmethylcellulose | 2.0 g |
| Propylene glycol | 1.0 g |
| High-maltose syrup | 40.0 g |
| Sorbitol | 20.0 g |
| Citric acid | 0.1 g |
| Polysorbate 80 | 0.1 g |
| Deionized water | q.s. to 100 ml |

EXAMPLE 18

Syrup formulation for oral administration

A syrup formulation was prepared using the ingredients shown below.

| | |
|---|---|
| Coated hydrocodone-resin complex of Example 11 | 2.02 g |
| Sodium benzoate | 0.3 g |
| Tragacanth gum | 0.68 g |
| Xanthane gum | 0.18 g |
| Propylene glycol | 1.0 g |
| High-maltose syrup | 40.0 g |
| Sorbitol | 20.0 g |
| Citric acid | 0.1 g |
| Polysorbate 80 | 0.1 g |
| Deionized water | q.s. to 100 ml |

EXAMPLE 19

Nasal spray formulation

A nasal spray formulation was prepared using the ingredients shown below.

| | |
|---|---|
| Coated PPA-resin complex of Example 6 | 6.45 g |
| Ethylparaben | 0.05 g |
| Hydroxypropylcellulose | 1.0 g |
| Polysorbate 80 | 0.1 g |
| Sodium chloride | 0.9 g |
| Deionized water | q.s. to 100 ml |

EXAMPLE 20

Eye drop formulation for instillation

An eye drop formulation for instillation was prepared using the ingredients shown below.

| | |
|---|---|
| Coated pilocarpine-resin complex of Example 12 | 6.50 g |
| Methylparaben | 0.10 g |
| Propylparaben | 0.02 g |
| Carbopol | 0.50 g |
| Mannitol | 4.0 g |
| Polysorbate 80 | 0.1 g |
| Deionized water | q.s. to 100 ml |

What is claimed is:

1. A prolonged-release liquid type of pharmaceutical preparation comprising:

(a) 0.1–45.0 w/v % of diffusion barrier-coated complex particles, which are prepared by adsorbing a pharmacologically active drug onto ion exchange resin particles to form drug-resin complex particles, treating the drug-resin complex particles with an impregnating agent to form treated complex particles, and then coating the treated complex particles with ethylcellulose, wherein said ethylcellulose has an ethoxyl group content of 44.0–47.5%;

(b) a preservative selected from the group consisting,
(i) one of para-hydroxybenzoic acid esters, wherein if methyl para-hydroxybenzoate is chosen, the preparation contains it at a concentration of 0.05–0.75 w/v %; if ethyl para-hydroxybenzoate is chosen, the preparation contains it at a concentration of 0.05–0.075 w/v %; if propyl para-hydroxybenzoate is chosen, the preparation contains it at a concentration of 0.03–0.05 w/v %; and if butyl para-hydroxybenzoate is chosen, the preparation contains it at a concentration of 0.01–0.015 w/v %;

(ii) a mixture of two or more of para-hydroxybenzoic acid esters, wherein if a mixture of methyl para-hydroxybenzoate and propyl para-hydroxybenzoate is chosen, the preparation contains the former at a concentration of 0.05–0.10 w/v % and the latter at a concentration of 0.01–0.02 w/v %, respectively; and (iii) sodium benzoate at a concentration of 0.1–0.5 w/v %; and the percent dissolution of the drug from the drug-resin complex changes minimally upon storage at 25° C. for a long period of time, (c) a solvent, wherein said preparation can be stably stored for a long time without loss of its controlled-release property.

2. The pharmaceutical preparation according to claim 1 wherein the pharmacologically active drug is selected from the group consisting of codeine, dihydrocodeine, dextromethorphan, phenylpropanolamine, methylephedrine, and hydrocodone.

3. The pharmaceutical preparation according to claim 1 wherein the ion exchange resin particles are a gel type divinylbenzene sulfonic acid cation exchange resin.

4. The pharmaceutical preparation according to claim 1 wherein the impregnating agent is polyethylene glycol.

5. The pharmaceutical preparation according to claim 1 wherein the ethoxyl group content of ethylcellulose is within 45.0–46.5%.

6. The pharmaceutical preparation according to claim 1 wherein 5.0–30.0 parts by weight of ethylcellulose is coated relative to 100 parts by weight of the impregnated complex particles.

7. The pharmaceutical preparation according to claim 1 wherein the preservative is methyl para-hydroxybenzoate.

8. The pharmaceutical preparation according to claim 1 wherein the preservative is ethyl para-hydroxybenzoate.

9. The pharmaceutical preparation according to claim 1 wherein the preservative is propyl para-hydroxybenzoate.

10. The pharmaceutical preparation according to claim 1 wherein the preservative is butyl para-hydroxybenzoate.

11. The pharmaceutical preparation according to claim 1 wherein the preservative is a mixture of methyl para-hydroxybenzoate and propyl para-hydroxybenzoate.

12. The pharmaceutical preparation according to claim 1 wherein the preservative is sodium benzoate.

13. The pharmaceutical preparation according to claim 1 which further contains a viscosity-increasing agent, pH-adjusting agent, sweetening agent, and/or flavoring agent.

14. The pharmaceutical preparation according to claim 1, wherein the solvent is an aqueous solvent.

15. The pharmaceutical preparation according to claim 1, wherein the solvent is an oily solvent.

* * * * *